US010502711B2

United States Patent
Zhu et al.

(10) Patent No.: US 10,502,711 B2
(45) Date of Patent: Dec. 10, 2019

(54) EMBEDDED OR CLIP-ON DEVICE FOR HEALTH MONITORING OF AN ARTICLE

(75) Inventors: Xiangdong Zhu, Dublin, OH (US); Peter V. Buca, Sandusky, OH (US); Isaac Shilad, Chagrin Falls, OH (US); Jay Lee, Mason, OH (US)

(73) Assignee: Parker-Hannifin Corporation, Cleveland, OH (US)

( * ) Notice: Subject to any disclaimer, the term of this patent is extended or adjusted under 35 U.S.C. 154(b) by 706 days.

(21) Appl. No.: 13/884,275

(22) PCT Filed: Nov. 10, 2011

(86) PCT No.: PCT/US2011/060131
§ 371 (c)(1),
(2), (4) Date: May 9, 2013

(87) PCT Pub. No.: WO2012/067931
PCT Pub. Date: May 24, 2012

(65) Prior Publication Data
US 2013/0233081 A1    Sep. 12, 2013

Related U.S. Application Data

(60) Provisional application No. 61/413,504, filed on Nov. 15, 2010.

(51) Int. Cl.
*G01G 19/02* (2006.01)
*G01G 19/00* (2006.01)
(Continued)

(52) U.S. Cl.
CPC ............... *G01N 29/04* (2013.01); *G01L 1/26* (2013.01)

(58) Field of Classification Search
CPC . F16L 2201/30; F16L 2201/10; F16L 11/127; F16L 25/01; G01M 5/0033;
(Continued)

(56) References Cited

U.S. PATENT DOCUMENTS 4,663,975 A * 5/1987 Parkinson ............... G01L 1/106
73/778
4,956,999 A * 9/1990 Bohannan ................ G01H 1/00
73/587

(Continued)

FOREIGN PATENT DOCUMENTS

| DE | 10 2007 012147 A1 | 9/2008 |
| EP | 0 185 650 | 6/1986 |
| FR | 2 919 050 | 1/2009 |

OTHER PUBLICATIONS

Santamaria, P. P. Pokharel and J. C. Principe, "Generalized correlation function: definition, properties, and application to blind equalization," in IEEE Transactions on Signal Processing, vol. 54, No. 6, pp. 2187-2197, Jun. 2006. doi: 10.1109/TSP.2006.872524.*

(Continued)

*Primary Examiner* — Natalie Huls
*Assistant Examiner* — Monica S Young
(74) *Attorney, Agent, or Firm* — Renner, Otto, Boisselle & Sklar, LLP

(57) ABSTRACT

A sensor (10, 80) for monitoring health of an associated article (A) (e.g., a fluid connector) including a sensing element (12, 84, 86) disposed along a length of an outer surface of the associated article, wherein the sensing element is configured to detect at least one physical property of the associated article and output an electrical signal in proportion to an amount of the physical property applied to the sensing element; and a mounting mechanism (14, 88) configured to secure the force sensing element to at least a portion of the outer surface of associated article.

18 Claims, 17 Drawing Sheets

(51) Int. Cl.
*G01G 23/36* (2006.01)
*G01N 29/04* (2006.01)
*G01L 1/26* (2006.01)

(58) Field of Classification Search
CPC .... G01M 3/18; G01M 5/0025; G01M 5/0066; G01M 5/0083; G01M 5/0091; G01N 2291/106; G01N 2291/0231; G01N 2291/0258; G01N 2291/02827; G01N 29/2475; G01N 29/2481; G01L 1/162; G01L 5/167; G01L 9/00; G01L 9/0022; G01B 5/30; G01P 15/0922
USPC .......................................................... 73/866
See application file for complete search history.

(56) References Cited

U.S. PATENT DOCUMENTS

| | | | | |
|---|---|---|---|---|
| 5,416,724 | A * | 5/1995 | Savic | F17D 5/06 702/51 |
| 6,370,964 | B1 | 4/2002 | Chang et al. | |
| 6,498,991 | B1 * | 12/2002 | Phelan | G01M 3/18 138/104 |
| 6,785,616 | B2 * | 8/2004 | Lung | G01H 1/00 702/138 |
| 7,261,002 | B1 * | 8/2007 | Gysling | G01F 1/708 73/861.42 |
| 7,590,510 | B2 * | 9/2009 | Kim | G01H 9/004 340/870.15 |
| 8,138,931 | B2 | 3/2012 | Keast et al. | |
| 8,378,659 | B2 * | 2/2013 | Scott-Carnell | G01M 5/0041 324/522 |
| 8,547,539 | B2 * | 10/2013 | Ramos | G01B 11/18 356/301 |
| 2005/0033545 | A1 * | 2/2005 | Gysling | G01F 1/34 702/138 |
| 2005/0050956 | A1 * | 3/2005 | Gysling | G01F 1/7082 73/753 |
| 2005/0125166 | A1 * | 6/2005 | Loose | G01F 1/3254 702/45 |
| 2006/0196252 | A1 | 9/2006 | Deckard | |
| 2006/0233485 | A1 * | 10/2006 | Allen | F17D 5/00 385/13 |
| 2006/0243051 | A1 | 11/2006 | Bui et al. | |
| 2007/0012112 | A1 * | 1/2007 | Kim | G01H 9/004 73/594 |
| 2007/0028219 | A1 * | 2/2007 | Miller | G05B 23/021 717/124 |
| 2007/0168341 | A1 * | 7/2007 | Nichols | G06F 17/30551 |
| 2008/0011091 | A1 * | 1/2008 | Weldon, Jr. | G01L 1/255 73/766 |
| 2010/0174495 | A1 * | 7/2010 | Pereira | F16L 11/127 702/34 |
| 2011/0049579 | A1 * | 3/2011 | Dumitru | B82Y 10/00 257/254 |
| 2011/0132098 | A1 * | 6/2011 | Ballandras | G01L 1/162 73/778 |
| 2011/0313671 | A1 * | 12/2011 | Nedilko | B61K 9/08 702/14 |
| 2012/0174676 | A1 * | 7/2012 | Nyffenegger | G01V 1/186 73/647 |
| 2012/0182835 | A1 * | 7/2012 | Davis | G01S 3/80 367/118 |
| 2018/0356371 | A1 * | 12/2018 | Giese | G01N 29/4445 |

OTHER PUBLICATIONS

International Search Report and Written Opinion dated Jun. 13, 2012 for corresponding International Application No. PCT/US2011/060131 filed Nov. 10, 2011.

Holland et al., "Layered Polymer Whole Structure Health Monitoring Using Capacitance Sensing", 2010 IEEE/ASME International Conference on Advanced Intelligent Mechatronics, Jul. 2010, pp. 943-946.

Kang et al., "Introduction to carbon nanotube and nanofiber smart materials", Composites: Part B: Engineering, vol. 37, No. 6, Jan. 2006, pp. 382-394.

European Examination Report dated Mar. 10, 2016 for corresponding European Application No. 11790697.4 filed Nov. 10, 2011.

\* cited by examiner

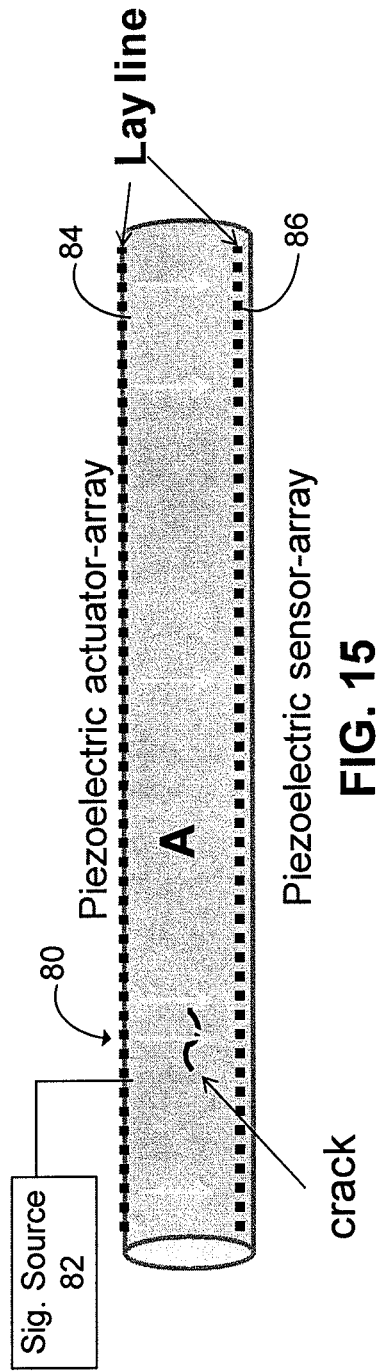
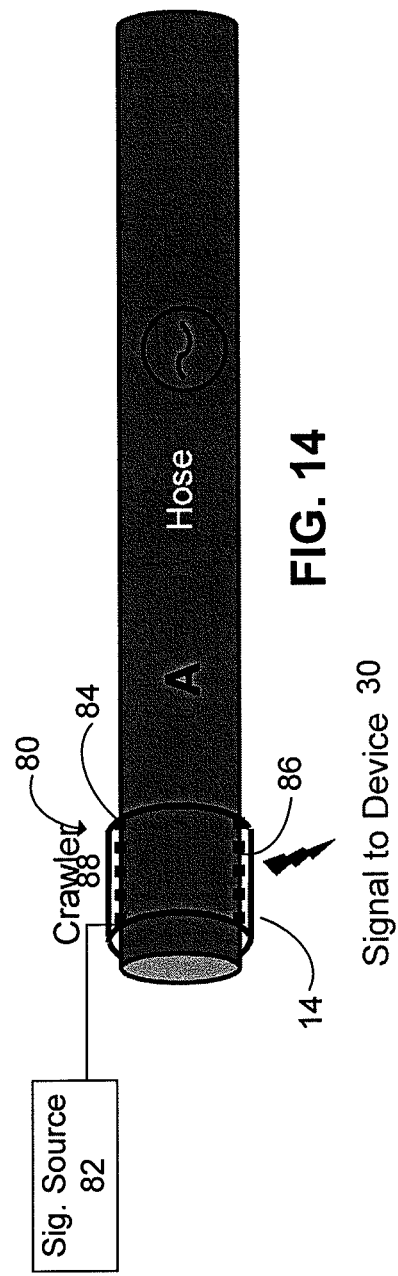
FIG. 15
FIG. 14

EMBEDDED OR CLIP-ON DEVICE FOR HEALTH MONITORING OF AN ARTICLE

This application is a national phase of International Application No. PCT/US11/60131 filed Nov. 10, 2011 and published in the English language.

RELATED APPLICATION DATA

The present application claims the benefit of the filing date of U.S. Provisional Patent Application Ser. No. 61/413,504 filed Nov. 15, 2010, which is incorporated herein by reference in its entirety.

TECHNICAL FIELD

The present invention relates to a sensor and a system for detecting damage to a pressurized article (e.g., a hydraulic hose).

BACKGROUND

A hydraulic connector hose is a tube that transfers fluids under pressure from one place to another. A hydraulic hose is a composite structure primarily made of rubber or thermoplastic and steel reinforcement. The steel reinforcement may include wire that is tightly wound spirally along the length of the hose so as to form a steel shell or it might be braided across the length of the hose for higher strength. The outermost covering is usually made of polymer material that helps protect the inner layers from harsh environments. Hydraulic hoses operate from a very low pressure to extremely high pressure depending on the applications. Hydraulic hoses are used in a variety of industries like heavy-machinery, household appliances etc and environments. In certain situations, especially in heavy machinery, the health of a hose is critical.

A hydraulic hose has a finite service life and all hoses eventually fail due to various factors like external damage, multi-plane bending, operating conditions, etc. The damage to a hose carrying such high pressures can lead to serious injury or death of an operator. Hence, monitoring the health of the hose becomes critical.

Hydraulic power systems are extensively used in many applications. The hydraulic hose is the "artery" that keeps equipment running. Consequences of hose failure are serious. It not only causes equipment downtime, but also environmental and safety issues. Current maintenance schemes are mainly based on preventive or Fail-and-Fix (FAF). A higher level of maintenance, Predict-and-Prevent (PAP) is needed to achieve near-zero down time maintenance, which in turn will increase productivity and safety.

SUMMARY

The present invention is directed to a sensor and system for use in detecting a failure in a pressurized article (e.g., a hydraulic hose).

One aspect of the invention relates to a sensor for monitoring health of an associated article, the sensor including: a sensing element disposed along a length of an outer surface of the associated article, wherein the sensing element is configured to detect at least one physical property of the associated article and output an electrical signal in proportion to an amount of the physical property applied to the sensing element; and a mounting mechanism configured to secure the force sensing element to at least a portion of the outer surface of associated article.

Another aspect of the invention relates to the sensor being built into the associated article.

Another aspect of the invention relates to a sensor for monitoring health of an associated article, the sensor including: a signal source; a first array of piezoelectric actuators disposed on an outer surface of the associated article, wherein the first array is coupled to the signal source and the piezoelectric actuators generate ultrasonic signals in response to the signal source, a second array of piezoelectric sensors disposed on the outer surface of the associated article, wherein the first array and the second array are spaced apart and the piezoelectric sensors detect the ultrasonic signals that propagate through at least a portion of the article; and a coupling member for mounting on at least a portion of the article, wherein the mounting member secures the first array of piezoelectric actuators and the second array of piezoelectric sensors on the article.

Other systems, devices, methods, features, and advantages of the present invention will be or become apparent to one having ordinary skill in the art upon examination of the following drawings and detailed description. It is intended that all such additional systems, methods, features, and advantages be included within this description, be within the scope of the present invention, and be protected by the accompanying claims.

It should be emphasized that the term "comprise/comprising" when used in this specification is taken to specify the presence of stated features, integers, steps or components but does not preclude the presence or addition of one or more other features, integers, steps, components or groups thereof."

BRIEF DESCRIPTION OF THE DRAWINGS

Embodiments of this invention will now be described in further detail with reference to the accompanying drawings, in which:

FIGS. 14-15 are another exemplary sensor in accordance with aspects of the present invention.

DETAILED DESCRIPTION OF EMBODIMENTS

Aspects of the present invention are directed to a system and a sensor for monitoring health of an associated article. For purposes of this disclosure, the associated article (A) may be a hydraulic hose or other hose-type member that is configured to transfer liquid through the member.

Figure 1:
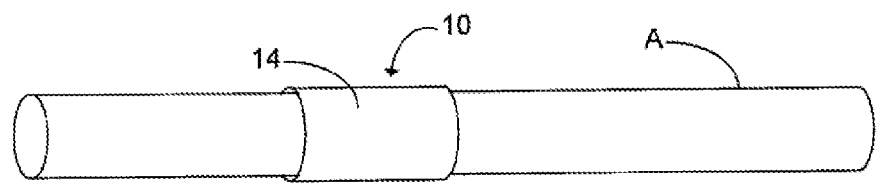
FIG. 1 is an exemplary sensor in accordance with aspects of the present invention.
Figure 2:
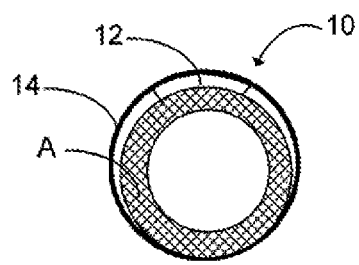
FIG. 2 is a cross-section of the sensor sleeve of FIG. 1 covering an article in accordance with aspects of the present invention.
Figure 3:
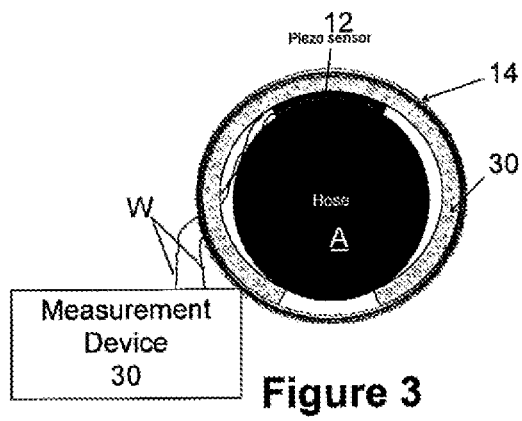
FIG. 3 is a cross-section of an exemplary sensor system in accordance with aspects of the present invention.

An exemplary sensor 10 for monitoring health of an associated article (A) is illustrated in FIGS. 1-3. The sensor 10 includes a sensing element 12 disposed along a length or circumference of an outer surface of the associated article (A). Alternatively, the sensing element 12 may be disposed within the associated article (A). The sensing element 12 is configured to detect at least one physical property associated with the article (A) and output an electrical signal in proportion to an amount of the physical property detected by the sensing element. For example, the sensing element may be configured to detect strain, stress, pressure, or any other physical characteristic that may provide an indication as to the health of the article (A). Exemplary sensing elements 12 include an electroactive polymer (EAP) that measures force, strain, pressure and/or stress generated between the mounting mechanism and the outer surface of the associated article, a piezoelectric material (e.g., polyvinylidene fluoride (PVDF)) that measures force, strain, pressure and/or stress generated between the mounting mechanism and the outer surface of the associated article, one or more strain sensors that measure deformation of the outer surface of the associated article (A).

Figure 4:
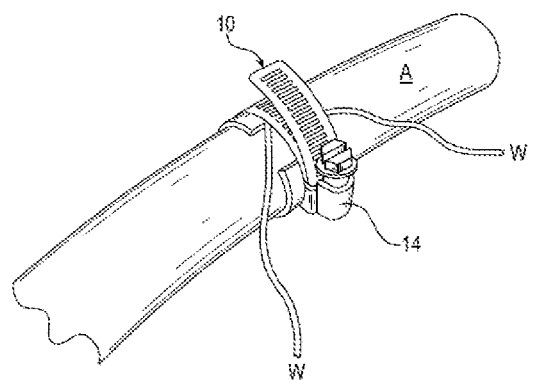
FIG. 4 is an exemplary embodiment of a sensor secured to an article in accordance with aspects of the present invention.

The sensor 10 includes a mounting mechanism 14 that is configured to secure the sensing element 12 to at least a portion of the outer surface of associated article (A). In a preferred embodiment, the mounting mechanism 14 may be releasably secured to the article (A). For example, the mounting mechanism 14 may be in the form of a hose clamp that may be tightened to secure the mounting mechanism and the hose clamp may be loosened to remove the mounting mechanism 14 from the article (A), as illustrated in FIG. 4. The mounting mechanism 14 may be releasably secured to the outer surface of the associated article in order to facilitate securing and/or removal of the sensor 10 to the associated article (A).

Figure 5:
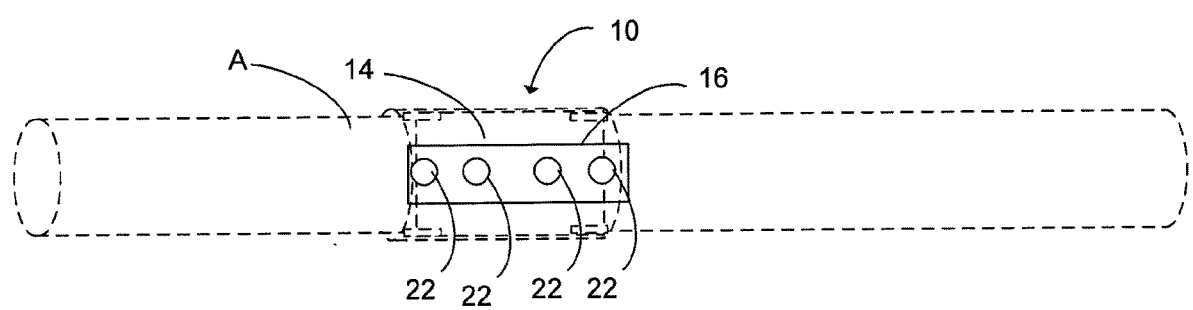
FIGS. 5-6 are schematic views of an exemplary sensor and drive mechanism in accordance with aspects of the present invention.
Figure 6:
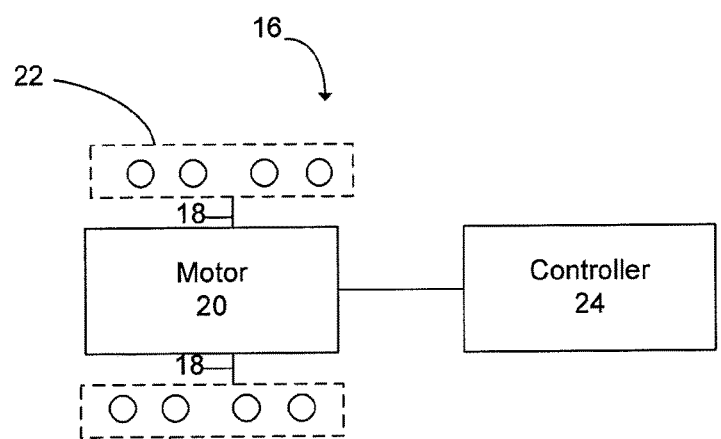

In one embodiment, the mounting mechanism 14 is coupled to a motion assembly 16. The motion assembly 16 is operable for moving the sensor 10 along a length of the associated article (A), as illustrated in FIGS. 5 and 6. Alternatively, the motion assembly 16 may be configured for moving the sensor 10 along or around the circumference of the associated article (A). The motion assembly 16 may include a drive mechanism 18 to facilitate movement of the sensor 10 along the article (A). The drive mechanism 18 may include a motor (or other force generating device) 20 that transfers a driving force to one or more movers 22 (e.g., wheels, ball-bearings, etc.), which facilitate movement of the sensor 10 along the article (A). Motion of the sensor 10 along the length of the article (e.g., hose) may be referred to herein as a "crawling" motion. The motion assembly 16 may be controlled by a controller 24 or other electronic or mechanical mechanism to move at a specified rate and direction (e.g., forward and/or reverse) along a section of the article and/or the entire length of the article (A). In addition, the motion assembly 16 may repeatedly crawl along a prescribed segment of the article to repeatedly determine health of the prescribed segment. The sensor array can also cover the entire length or a portion of the article. In such cases, motion of the assembly 16 may not be necessary.

Referring back to FIG. 3, the sensor 10 may include a deformable dielectric layer 30, which is configured to cover at least a portion of the associated article (A) and the force sensing element 12. The deformable dielectric layer 30 may be adhesively affixed to at least a portion of the mounting mechanism 14 in order to secure the deformable dielectric layer 30 to the mounting mechanism 14. In another embodiment, the sensing material 12 may also be adhesively affixed to at least a portion of the deformable dielectric layer 30. In yet another embodiment, the sensing element 12 may be supported by the deformable dielectric layer 30 and the dielectric layer is operable to conform to at a portion of the outer surface of the associated article (A). One function of the deformable dielectric layer 30 is to ensure the clamping force applied by the mounting mechanism 14 to secure the sensor 10 to the article (A) does not damage the sensing element 12. A suitable deformable dielectric layer may be rubber, plastic or silicone material.

In order to communicate electrical signals from the sensing element 12, one or more wire leads (W) may be coupled to the sensing element, as illustrated in FIGS. 3 and 4. The wire leads (W) are configured to output the electrical signal generated from the sensing element 12 to another device 31.

Figure 7:
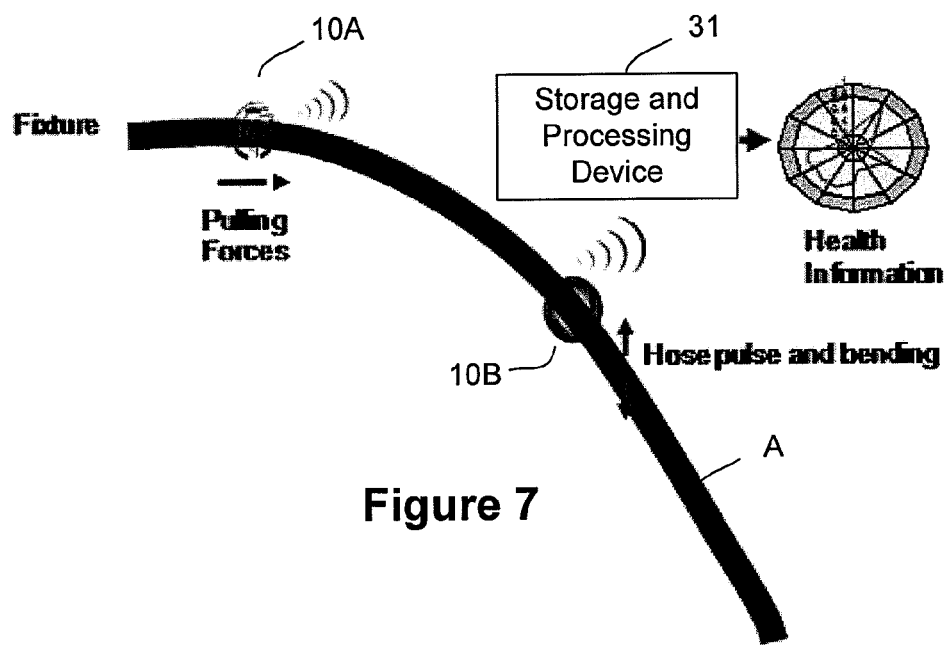
FIG. 7 is an exemplary system in accordance with aspects of the present invention.

The device 31 may be coupled wirelessly through a suitable adapter coupled to the wire leads (W), for example, to an external device 31, as illustrated in FIG. 7. In FIG. 7, the article (A) includes two sensors 10A and 10B for monitoring health of the article. The sensors 10A and 10B may wirelessly output signals to device 31, which may be storage device and/or a watchdog agent, such as an IMS Watchdog Agent, for example. The device 31 may store and/or process the received signals to determine health of the associated article (A). Alternatively the wire leads (W) may be coupled directly to the device 31, as illustrated in FIG. 3.

Figure 8:
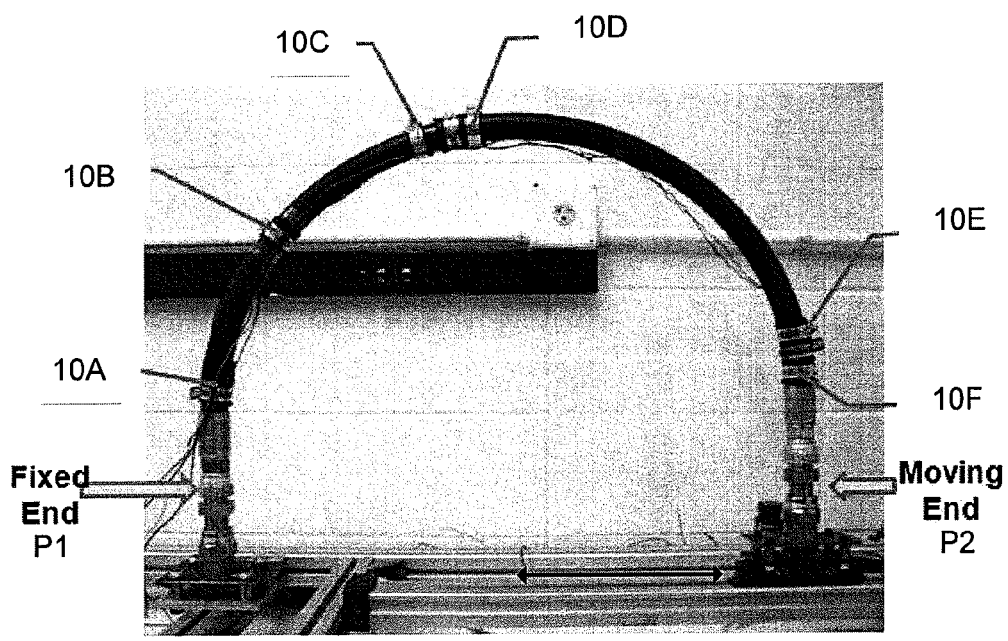
FIGS. 8 and 11 are exemplary testing rigs for testing sensors in accordance with aspects of the present invention.

An experimental set-up testing the feasibility of multiple sensors 10 on an associated article is illustrated in FIG. 8. Referring to FIG. 8, the article (A) is attached to two end points P1 and P2. End point one (P1) is fixed and end point two (P2) is configured to move in a direction to generate a bending force on the associate article. As end P2 moves from one position to another, the article (A) is exposed to fatigue and wear. In FIG. 8, there are six (6) sensors (10A-10F) spaced along the length of the article (A). Each of the sensors 10A-10F monitors a portion of the article, for example, the portion of the article that each sensor is covering. Each of the sensors 10A-10F are clip-on sensors and the sensing element 12 is oriented in two different directions, e.g., one in the longitudinal direction along the hose and one in the circumferential direction.

A National Instruments NI 9215 data acquisition module is used to acquire the voltage response from the sensing elements 12A-12F, corresponding to sensors 10A-10F, respectively. A sampling rate of 500 Hz is used for the data acquisition of the signal, and the bending moment was applied at a rate of 1 Hz. The signals received from the sensors 10A-10F are then filtered and an algorithm for counting strain cycles, as well as a data preprocessing step for the feature extraction and further data analysis is performed. A Finite Impulse Response (FIR) band-pass filter with a lower cutoff frequency of 0.5 Hz and an upper cutoff frequency of 1.5 Hz is used to smooth the raw time signal. The filtered signal as well as the frequency domain spectrum of the time signal is compared for the response at each sensor location.

Referring to FIG. 8, in sensors 10A, 10B, 10C and 10F, the sensor orientation is in the circumferential direction. Sensors 10D and 10E had sensor orientation are placed in the longitudinal direction. The signal response at sensors 10A, 10B and 10F had a higher level of noise compared to the other three signals and lower amplitude. The response of sensors 10C, 10D and 10E have a higher signal to noise ratio. A comparison between the amplitude of the signals is shown below in Table 1.

TABLE I

Amplitude Level at Locations #3-5 on Bending Test Rig

| Sensor Location | Amplitude Level (V) |
|---|---|
| Location # 3 | 0.08 |
| Location # 4 | 0.45 |
| Location # 5 | 0.50 |

Figure 9:
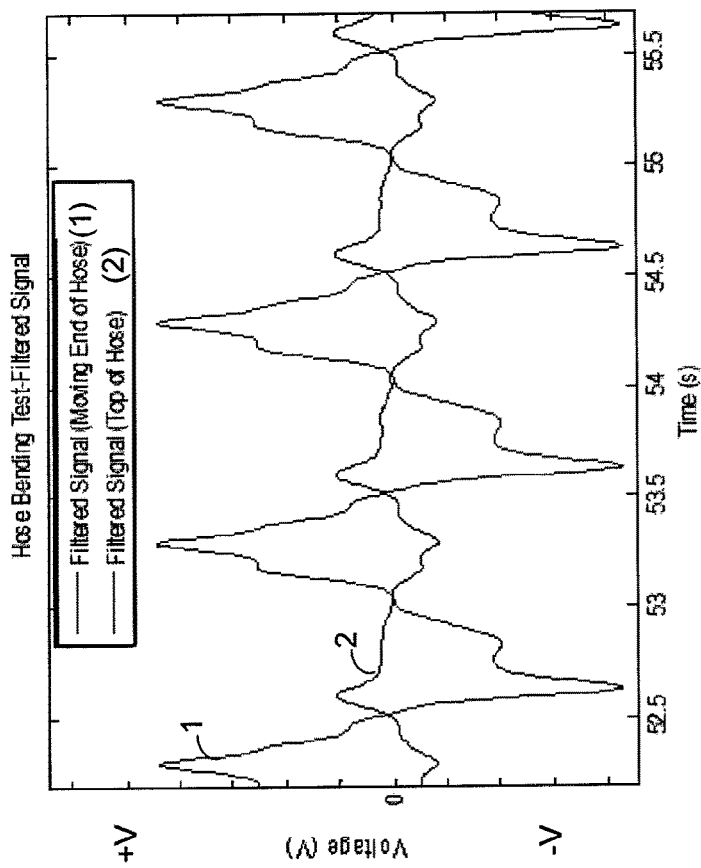

A counting algorithm was developed that monitored change in sign of the slope of the filtered received signal. As illustrated in FIG. 9, the filtered signal includes a periodic waveform and the instance when the slope changes from positive to negative indicates a peak in the waveform. For each instance an upper peak in the waveform occurs, the counter is incremented. Overall the best response is determined to be at sensors 10D and 10E. Thus, it is concluded that for the bending motion, the longitudinal orientation for the sensor 10 provides the best signal, and the sensors closer to the moving end has a larger response.

Figure 10:
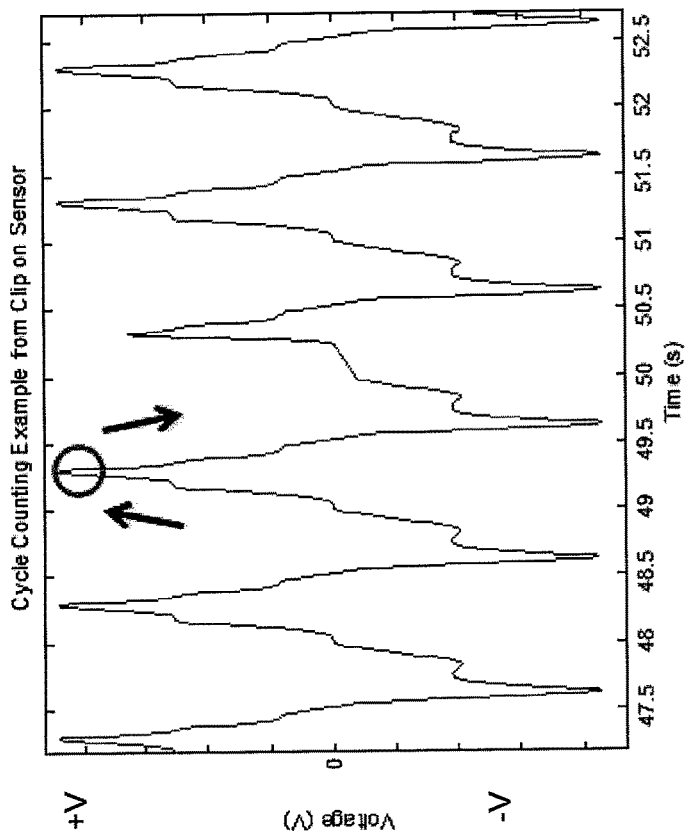
FIGS. 9-10 are exemplary results from the system of FIG. 8.

The counting algorithm utilizes a slope based cycle counting method. An exemplary slope-based counting method is summarized in the following steps listed below:

1. Filter and smooth the time domain signal.
2. Take numerical derivative of filtered signal and detect peak by looking at point when the slopes goes from positive to negative. For example, see FIG. 10.
3. The peak detection might pick up short dips, so a criteria needs to be set to consider only points of at least a certain value (cutoff-value).

Another counting method tested is commonly referred to as a zero-crossing method. The zero-crossing method contains simple logic to detect an instance in which the waveform is zero and this would indicate half a cycle. The zero crossing method logic is similar to the slope based method, however the instance in which the filtered signal goes from positive to negative or negative to positive, a half cycle count increment is made. A person of ordinary skill in the art will appreciate that the counting methods described above are exemplary in nature and other counting mechanisms may be used in accordance with aspects of the present invention.

A data set consisting of 131.7 seconds worth of filtered data is used to test both counting algorithms and the results are shown in Table 2. Note that the bending being applied to the hose placed in the test-rig was approximately 1 cycle/sec, so both counting methods compare well to the theoretical number of cycles.

TABLE 2

Cycle Counting Results

| Theoretical # Cycles | Slope Counting Method | Zero Cross Counting Method |
|---|---|---|
| 131.7 s * 1 cycle/sec = 131.7 | 130 cycles | 132 cycles |

A real-time cycle counting algorithm is implemented using a slope based counting method. This methodology incorporated tuning parameters, e.g., a cutoff (or threshold) value, in order to tune ensure that the counting algorithm did not detect erroneous small peaks due to noise or other small signal fluctuations.

Figure 11:
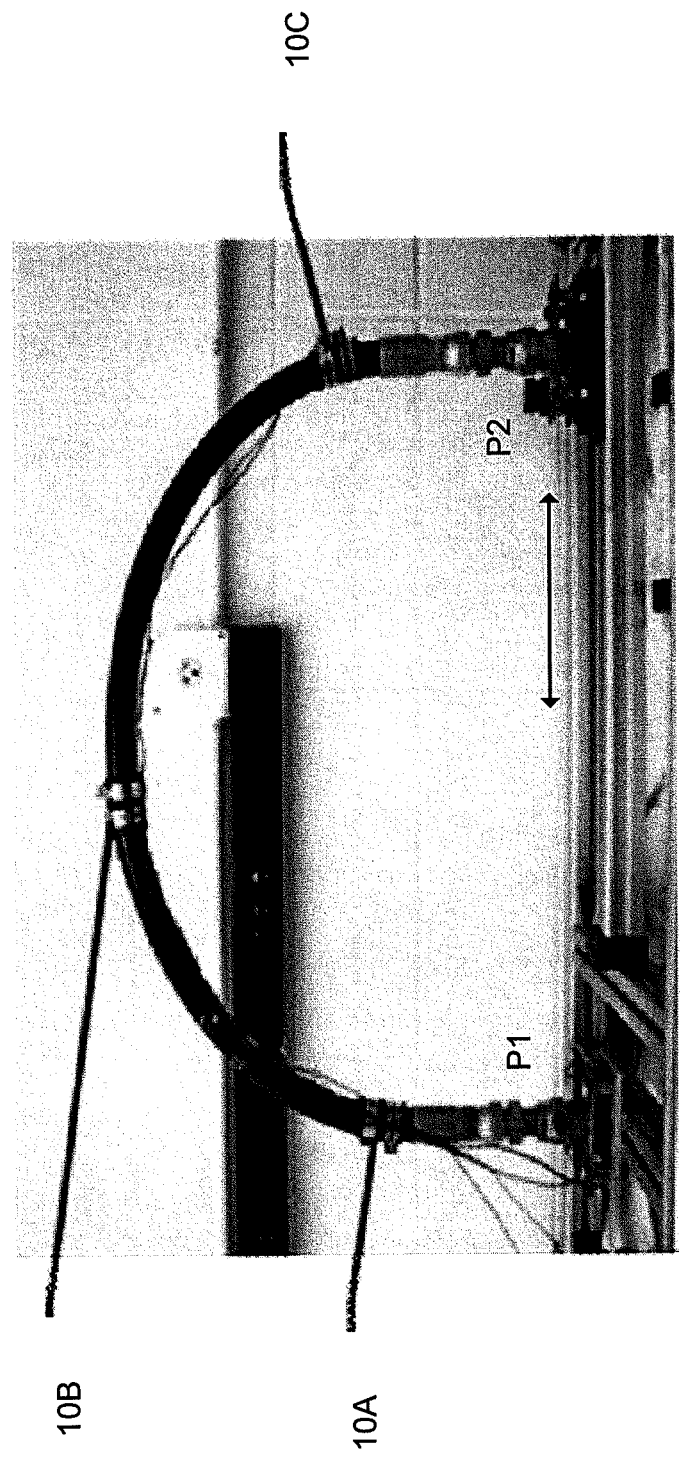

Referring to FIG. 11, three (3) clip-on sensors 10 having a PVDF piezoelectric sensing element (identified as 10A, 10B, and 10C) are placed in the longitudinal direction along the article (A) with one near the fixed end P1 (e.g., sensor 10A), one in the middle of the hose (e.g., sensor 10B) and one near the moving end P2 (e.g., sensor 10C)). The bending test-rig is used and data is collected for a 1-hour time-span from both a healthy and a hose with damage in the wire layer in the middle section of the hose. Different time domain and frequency domain features are extracted from each 2500 block of data for of the 3 sensor signals. For each sensor signal, 10 features are extracted, which provide a total of 30 features extracted from the data. Exemplary extracted features include maximum amplitude of the waveform, minimum amplitude of the waveform, root mean square (RMS) value of the waveform, period of the waveform, frequency domain peak, etc.).

Figure 12:
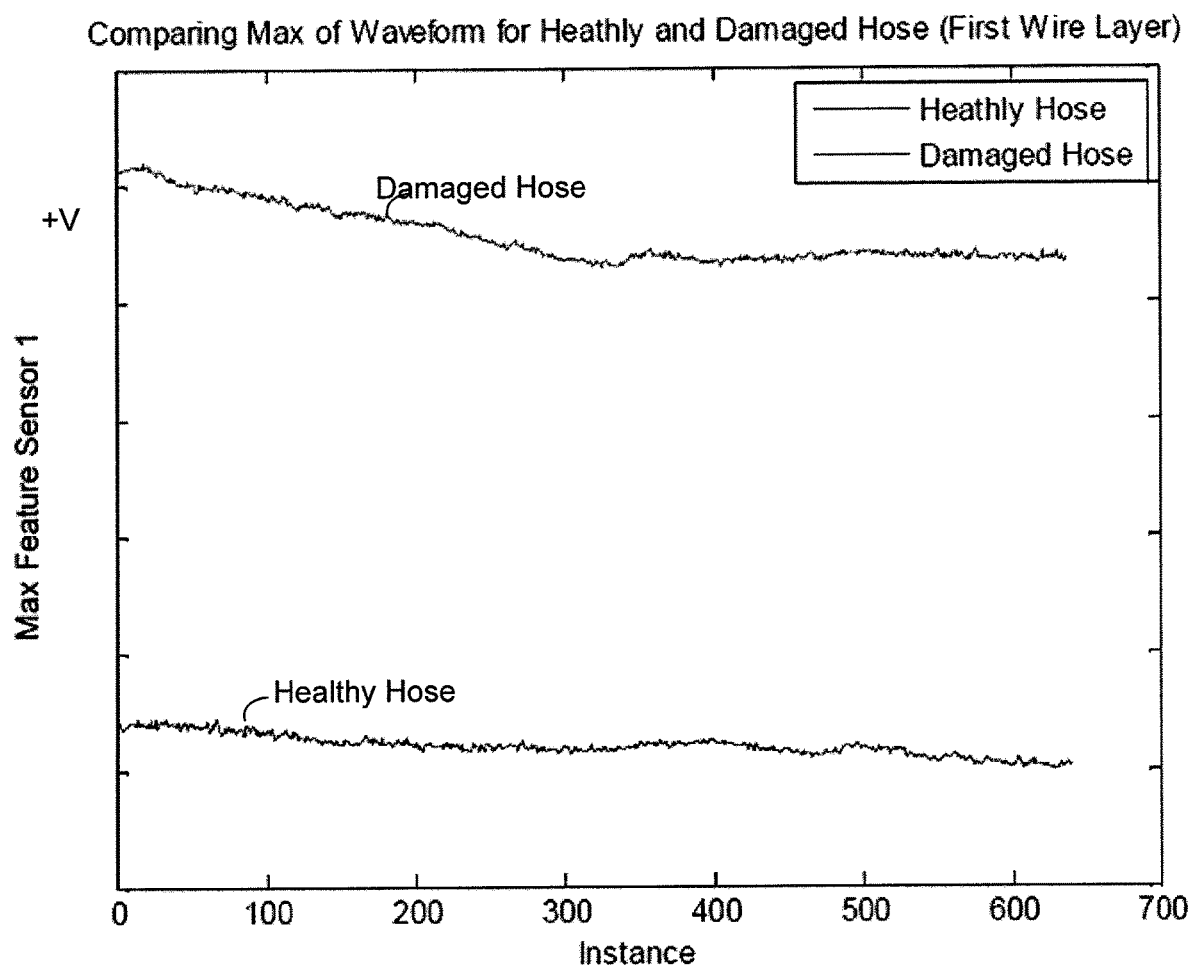
FIGS. 12-13 are graphical results from testing sensors illustrated in FIG. 11.

One of the features that shows much difference between the data sets collected from the healthy and damaged hose is the maximum value of the waveform. An exemplary plot of this feature is shown in FIG. 12. As illustrated in FIG. 12, this feature is larger for the damaged hose compared to the data collected from the healthy hose. Features such as the RMS of the waveform, minimum value of the waveform, the frequency domain peak at 1 Hz, also shows similar clear differences between the damaged and healthy hose. Variability in the clamping force that is used to attach the sensor to the hose surface as well as other factors make it difficult to determine whether the difference in the features is due to damage in the hose alone or may also be caused by variation in clamping force.

Further testing was done to further investigate the feasibility of extracting features from the PVDF sensor signal. In this particular testing, a healthy hose was used to initially collect data, then an induced failure is placed in the healthy hose without removing the sensors, and the same amount of data was collected after inducing the damage. In this particular instance the same experimental setup regarding sensor location in FIG. 11 was used. In this testing data was collected for a healthy hose undergoing bending, for 3 data sets that are 1.5 hour time-span each. An anomaly (e.g., a cut) was then introduced at both ends of the article (e.g., a rubber hose). The same data acquisition procedure discussed above was used. A 20 minute waiting period was used between each two data sets collected, in order to provide a cool-down period.

Figure 13:
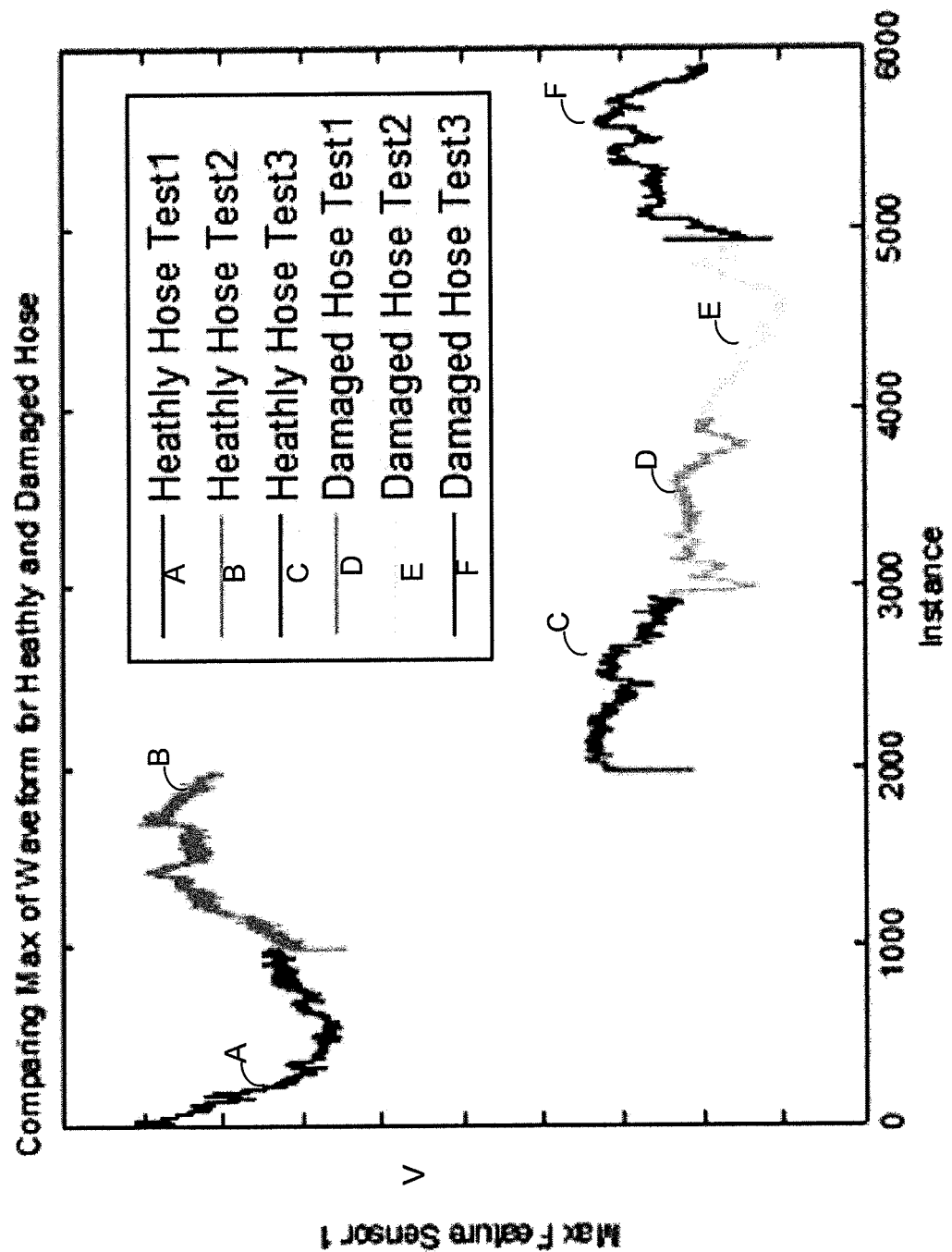

The same feature extraction methods discussed above were also used to examine this data. The maximum of the waveform signal is shown in FIG. 13 for the six (6) different tests; the initial three (3) tests for the healthy hose and the last three (3) tests after damaged was inducted. The maximum of the waveform from the PVDF sensor (e.g., sensor 10A) located at the fixed end P1 shows a decreasing trend and it drops from test 2 and 3, however it is difficult to see a difference from this feature in the data prior to and after the hose has damage (test 3 and test 4). Also considering that the feature undergoes upward and downward trends during the duration of a single test makes it very difficult to conclude whether any change is due to the damage induced, or other factors such as the influence of temperature or a change in clamping force.

Another embodiment of a sensor 80 in accordance with aspects of the present invention is illustrated in FIGS. 14 and 15. In operation, the sensor 80 includes of arrays of tiny piezoelectric elements. Some elements act as an actuator to produce ultrasonic waves, others act as receivers to receive the waves. If there is crack or other damage in the path between the actuator and the sensor, the ultrasonic waves received will be distorted. Thus, the sensor 80 may be used to detect local fatigue at a micro level in a structure.

The sensor 80 may be a clip-on device, as illustrated in FIG. 14 and/or the sensor 80 may be formed in the article (A) (e.g., between the lay lines of the article), as illustrated in FIG. 15. In FIGS. 14-15, the sensor 80 includes: a signal source 82; a first array of piezoelectric actuators 84 disposed on an outer surface (S) of the associated article (A). The first array of piezoelectric actuators 84 are coupled to the signal source and the piezoelectric actuators generate ultrasonic signals in response to the signal source. A second array of piezoelectric sensors 86 are disposed on the outer surface (S) of the associated article, wherein the first array and the second array are spaced apart and the piezoelectric sensors detect the ultrasonic signals that propagate through at least a portion of the article. The sensor 80 further includes a coupling member 88 for mounting on a portion of the article (A), wherein the mounting member secures the first array of piezoelectric actuators 84 and the second array of piezoelectric sensors 86 to the article. The piezoelectric actuators and sensor can also be arranged in such a way that the signals propagate longitudinally on the article (A) instead of circumferentially. In such case, the actuators are arranged circumferentially on the article (A) and the sensors are arranged circumferentially on the article (A), with a space between the two arrays to cover at least one portion of the article (A). Preferably, the signal source 82 is embodied in the crawler.

The coupling member 88 may be coupled to a motion assembly for traversing the sensor along a length of the article (A), as discussed above with respect to the motion assembly 16.

In one embodiment, the first array of piezoelectric actuators 84 is configured to generate the ultrasonic waves through at least a portion of the associated article. The signal source 82 may output a constant amplitude signal to the first array of piezoelectric actuators. In addition to or alternatively, the signal source may output a linearly varying amplitude signal to the first array of piezoelectric actuators. The second array of piezoelectric sensors 86 are configured to receive the ultrasonic waves and output a signal that corresponds to vibration detected during propagation of the ultrasonic wave through the surface of the associated article between the first array of piezoelectric actuators and the second array of piezoelectric sensors.

A storage device 31 or other electronic device may be coupled to at least the second array of piezoelectric sensors 86. Preferably, the storage element 30 is configured to store an output signal generated by the second array of piezoelectric sensors 86. Data obtained from the sensor 80 may be analyzed in a manner similar to that described above with respect to sensor 10. Furthermore, inter-sensor analysis may also be used to view additional properties of the article.

In order to enhance the functionality of the clip on sensor 10 and 80, it may be desirable to utilize one or more accelerometers. The accelerometers may provide information about acceleration of the hose during pressure changes, for example. A suitable accelerometer may be an ADXL 78 accelerometer.

Figure 16:
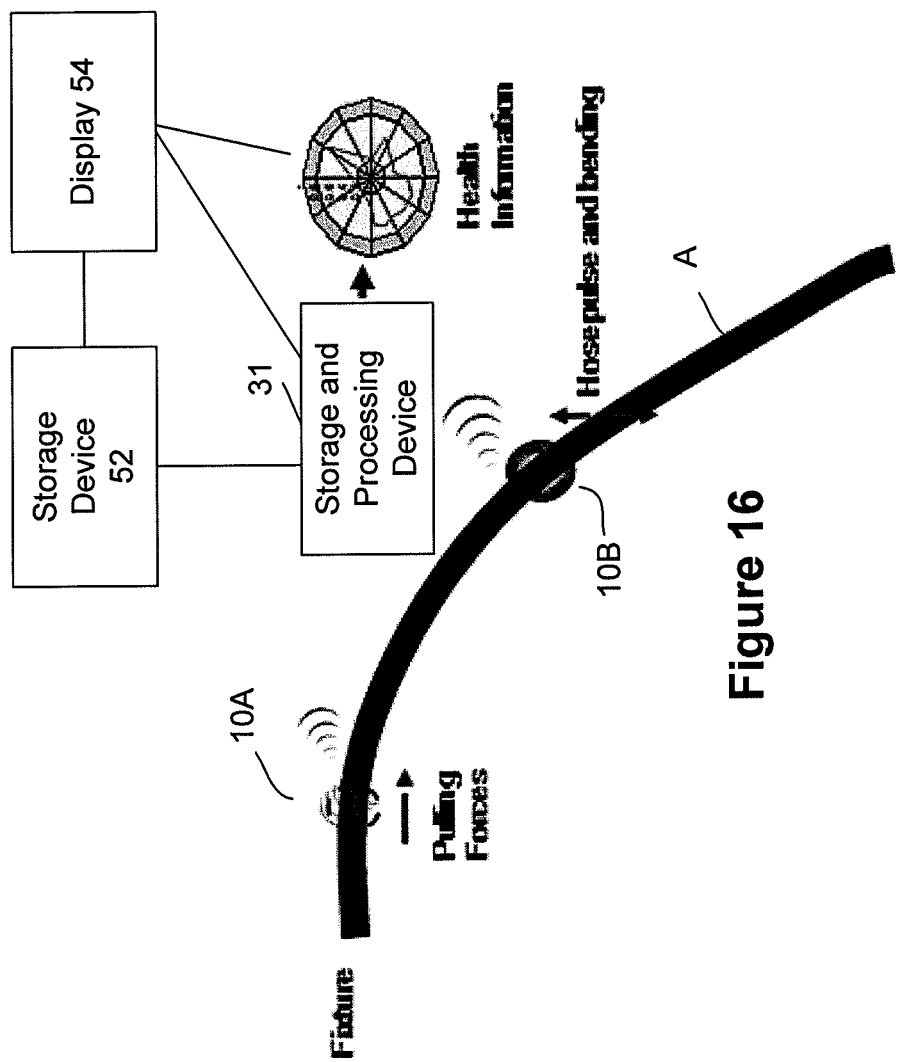
FIG. 16 is another exemplary system in accordance with aspects of the present invention.

Referring to FIG. 16, an exemplary system 50 for determining health of the associated article (A) includes sensors 10A and 10B disposed on along a portion of the article, a storage and processing device 52 and a display 54 coupled to the storage device. For purposes of brevity the following discuss implementation with sensor 10, but the system may also be implanted with sensor 80.

The sensor 10 may be one or more clip-on sensors that are configured to provide health information data associated with the article (A) to the storage device 31. The data received by the storage device 52 may be analyzed in accordance with an algorithm or any desired methodology executed by a processor 52. The storage device 52 is configured to store the output of the sensing element 12 (or piezoelectric sensors 86) and the storage device further includes reference data for use in determining the health of the article. The display 54 displays the health information of the associated article in a way that is suitable to the end user. FIG. 16 shows an exemplary display of a radar chart. Multiple articles' health information represented as 0-1 value is displayed on the radar chart, with each spider node as one article. As the health information of one article approaches 1, it is entering into the "warning" zone represented as pink color. Users can track each article and take appropriate actions for the articles entering into the warning zone. The warning zone can be modified based on users' confidence, for example, a warning zone may be between 0.8-1.

In summary, this technology can be used for hose prognosis (e.g., article health monitoring) in two embodiments, embedded in the article or a clip-on device that secures to the article. For example, in one embodiment, illustrated in FIG. 15, an array of piezoelectric actuators can be placed under the lay line; an array of piezoelectric sensors can also be place under the lay line on the other side of the hose. When a local crack or anomaly occurs, information will be received by comparing the difference of the receivers' signals.

In another embodiment, illustrated in FIGS. 2-4 and 14, a hose crawler is designed to inspect the hose section by section. The crawler is comprised of a sensing material that detects a physical property associated with the article in the sensor is secured. The crawler travels through the length of the article. At each section, the signal received from the sensors is recorded to a device either wirelessly or on its embedded chip. The signal then is compared with previous inspection data and or reference data to find any distortion or deviation in its features.

Figure 17:
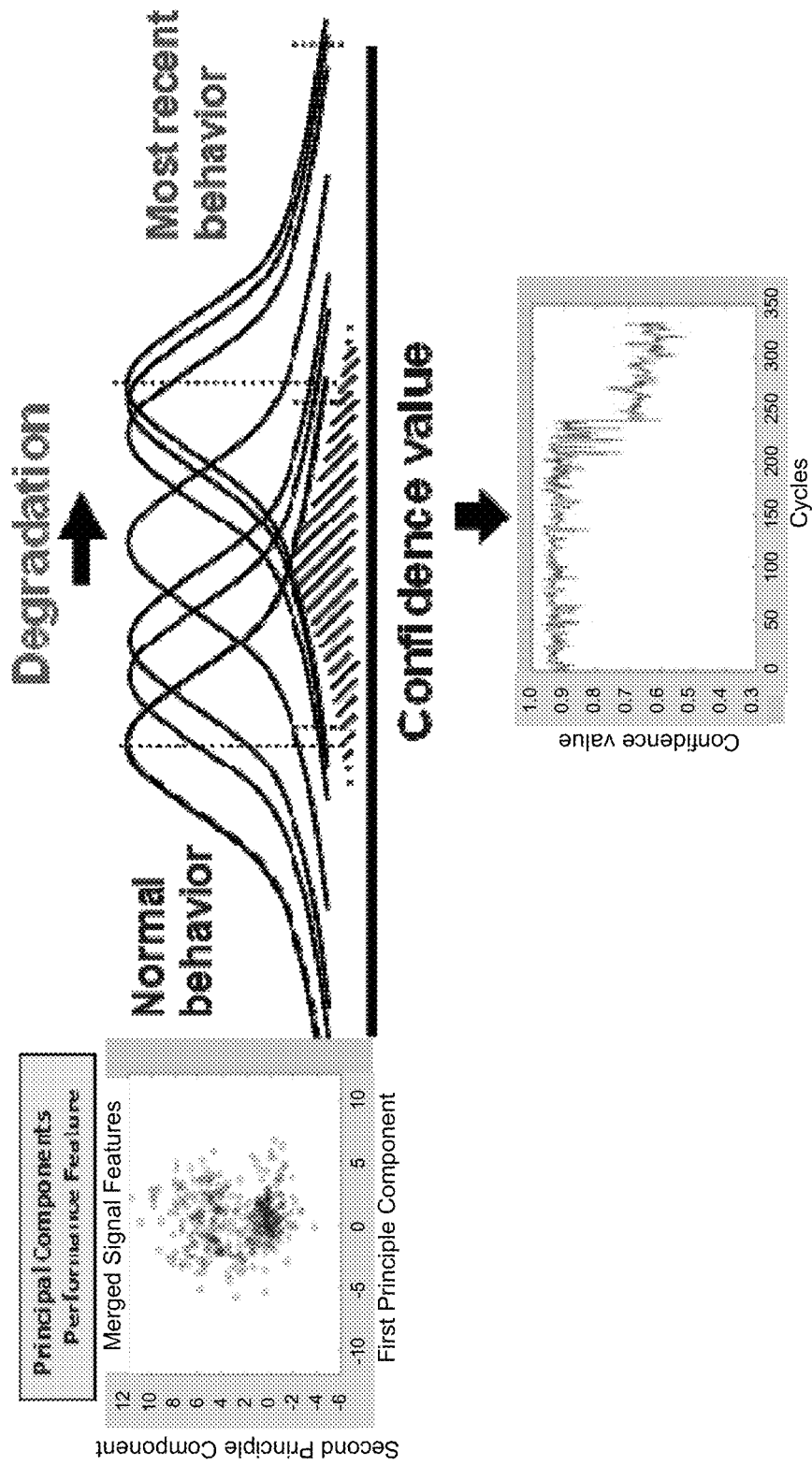
FIG. 17 is an exemplary chart illustrating article degradation.

The response of sensor is recorded and processed realtime. Based on the deviation trend of feature distribution, the degradation of article (e.g., hose) can be monitored, as illustrated in seen in FIG. 17. The degradation trend can be represented as 1 to 0 confidence value (CV). When CV is 1, it means the distribution of most recent behavior is almost identical with the normal behavior; when CV is 0, it means the distribution of most recent behavior has been moved away from normal behavior distribution.

For proof of concept testing, an experiment utilizing LDT0 piezoelectric film from Measurement Specialties placed on ends of a hose was performed. One film was used as an actuator to generate an ultrasonic wave; the other is to receive the wave as output. A chirp signal was generated and sent to the piezoelectric film. The wave propagates through the medium (hose) and the response is captured on the other end of the hose (output) by another piezoelectric film. The chirp signal was generated by two techniques: Using Lab-VIEW (constant amplitude) and using signal generator (Linearly increasing amplitude). The chirp signals were amplified and sent to the PZT films via a Piezo amplifier.

Figure 18:
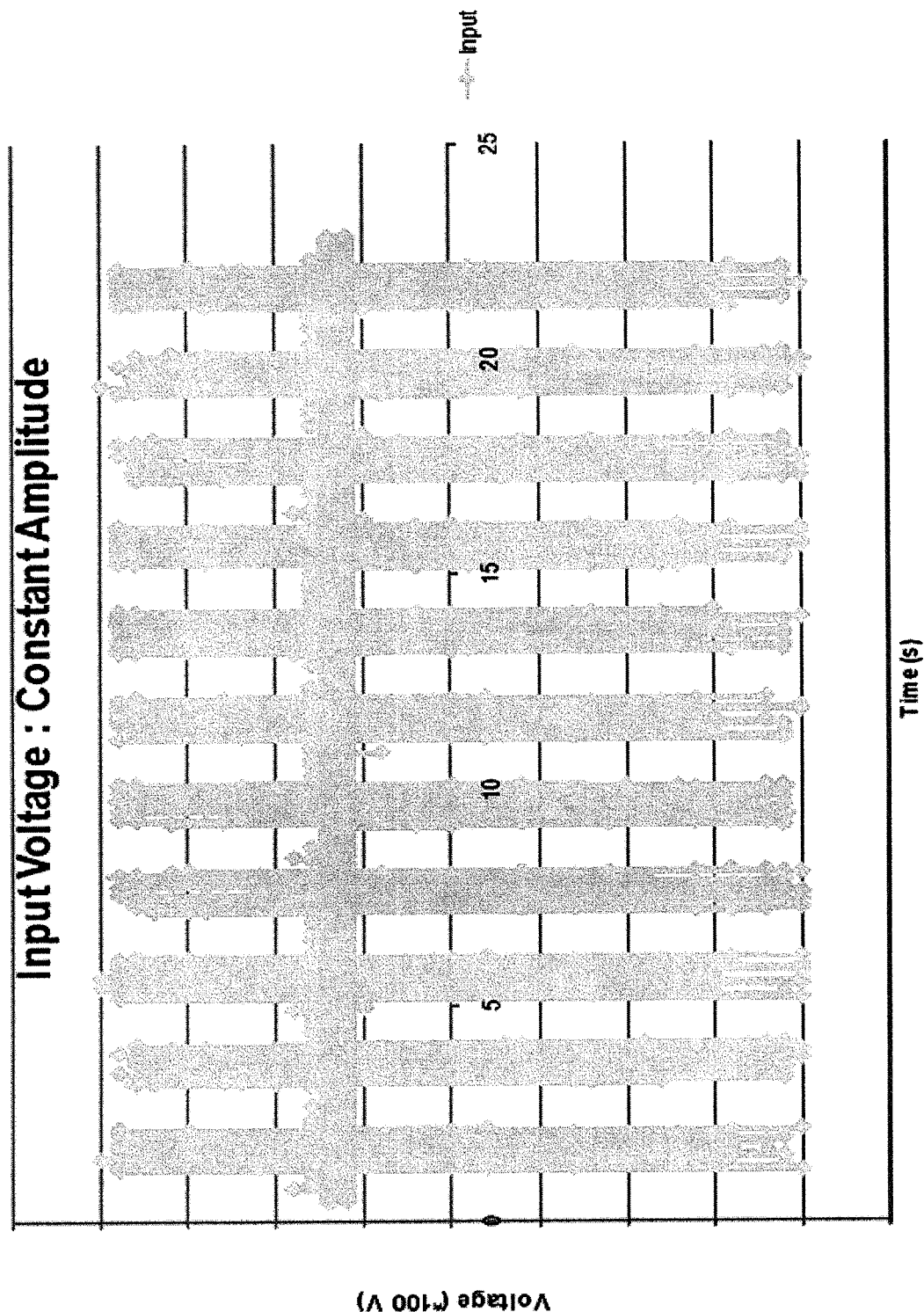
FIG. 18 is an exemplary chart illustrating constant amplitude input in accordance with aspects of the present invention.
Figure 19:
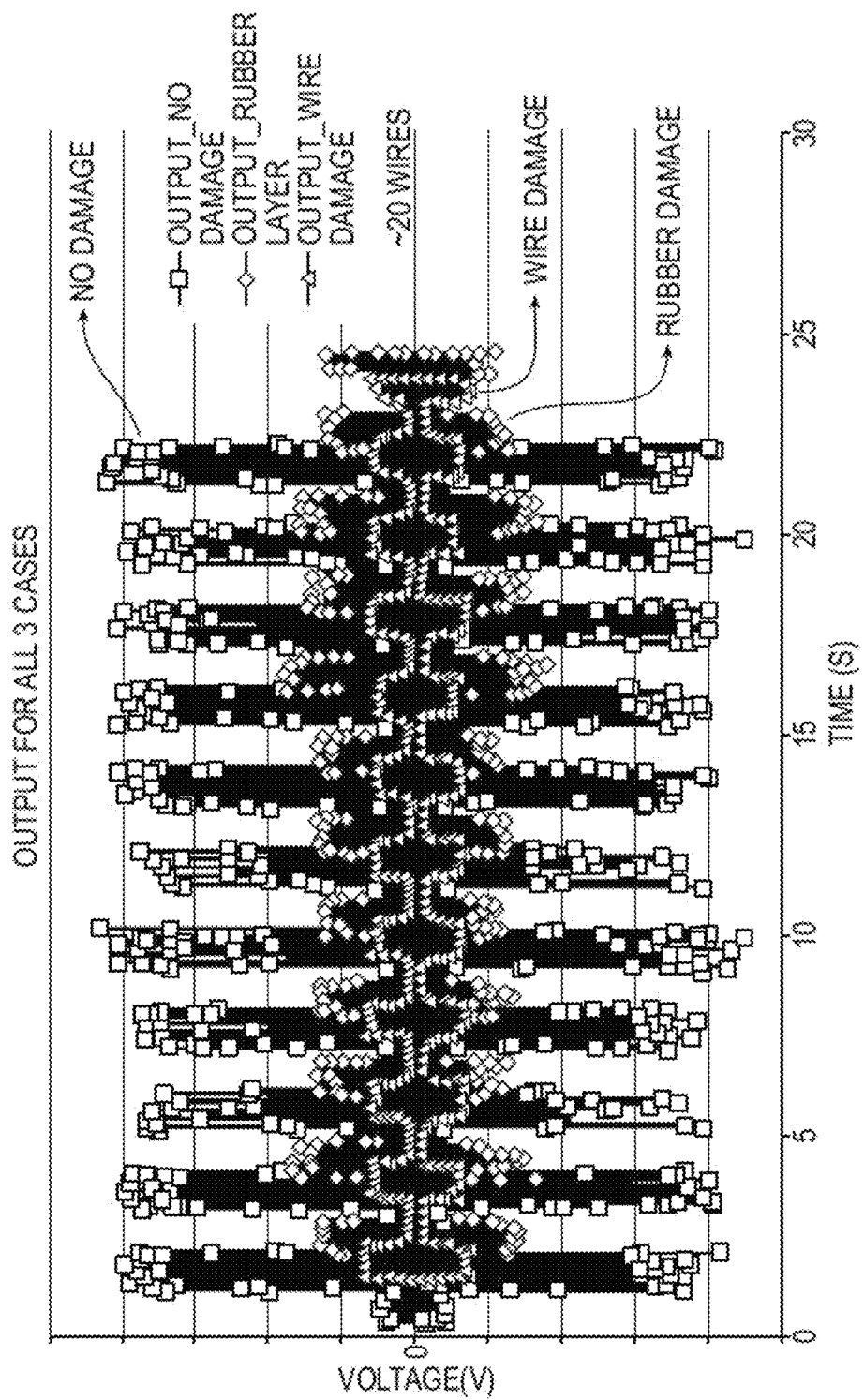
FIG. 19 is an exemplary chart illustrating various conditions of an article under test.
Figure 20:
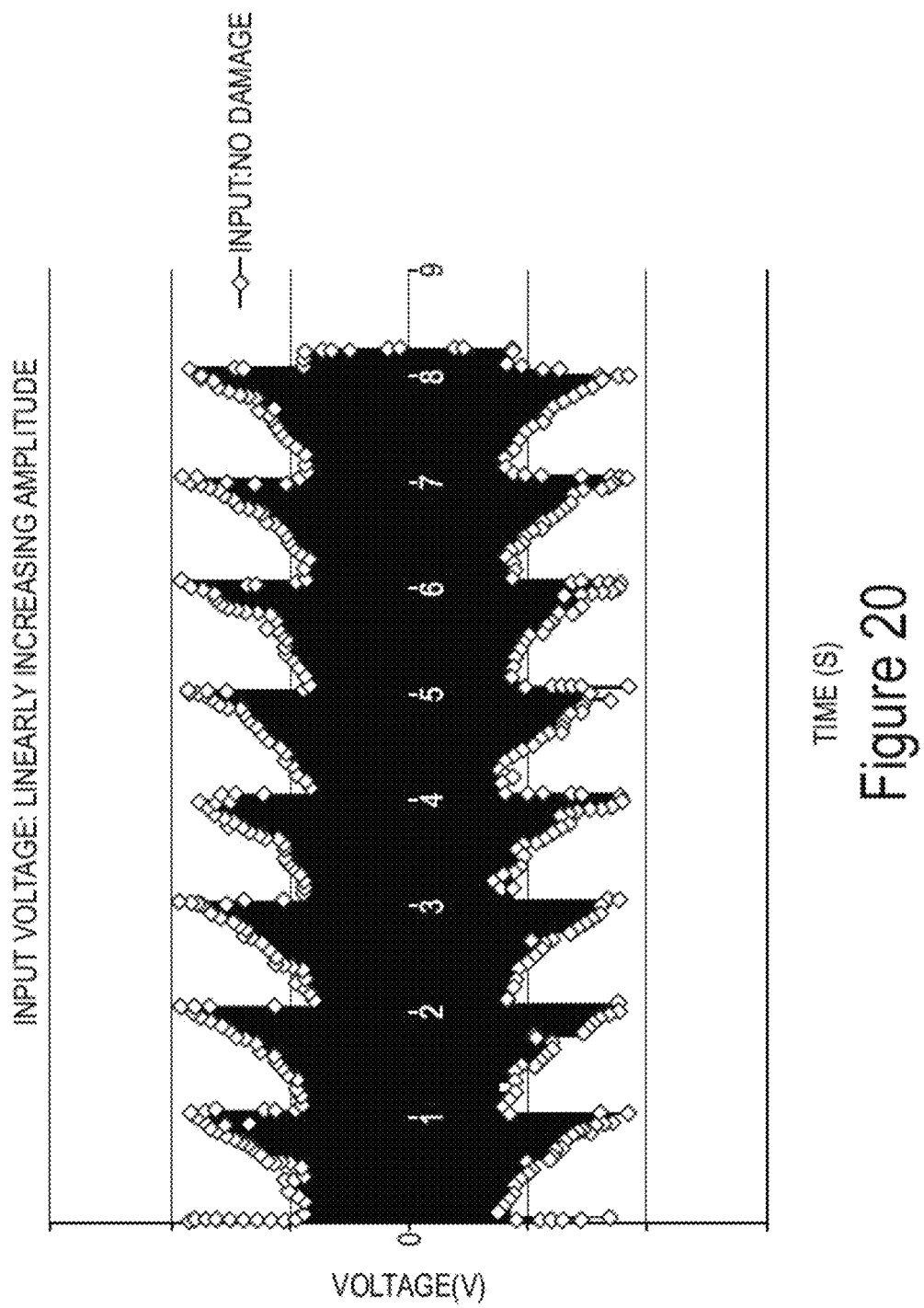
FIG. 20 is an exemplary chart illustrating linearly increasing amplitude input in accordance with aspects of the present invention.
Figure 21:
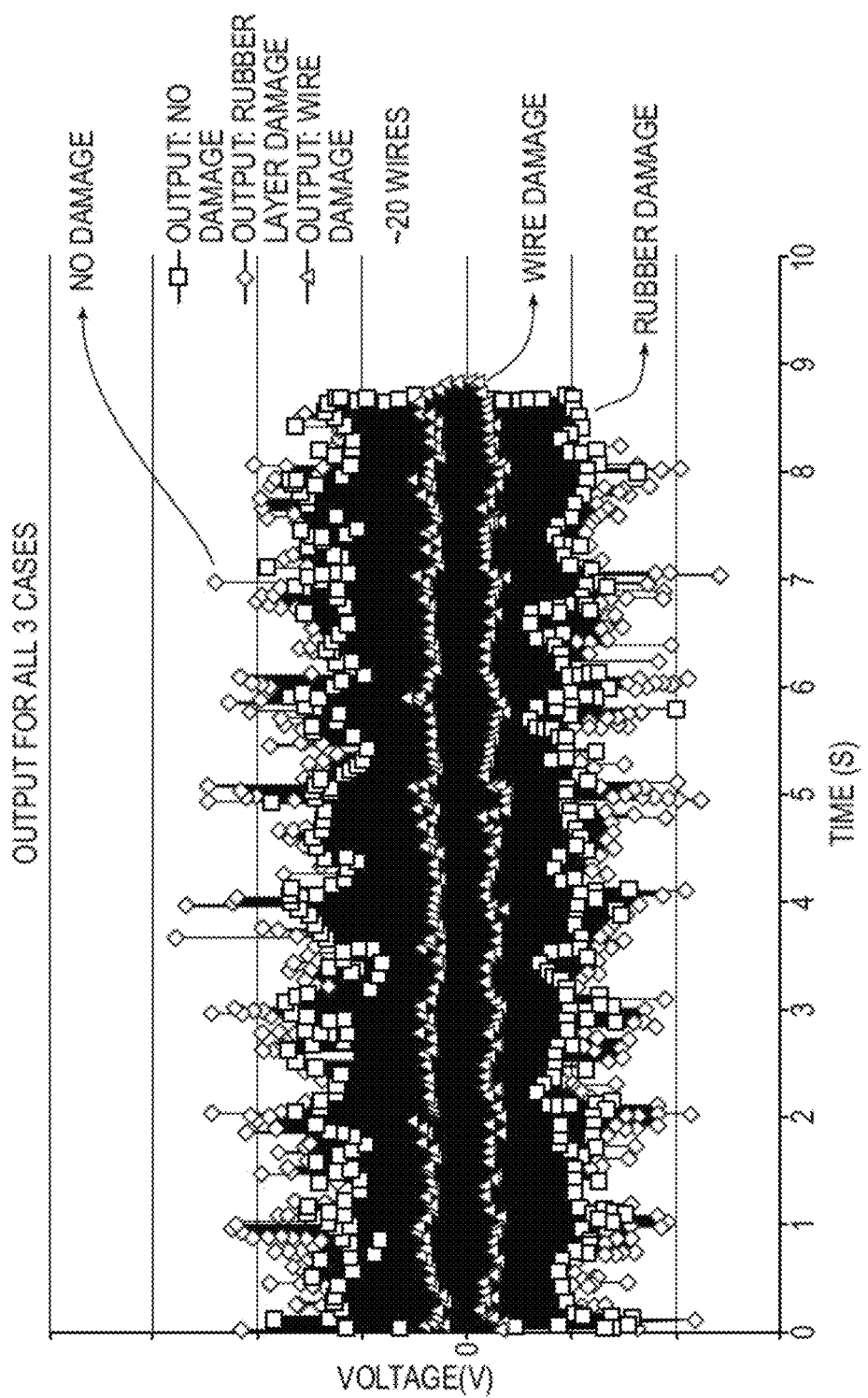
FIG. 21 is an exemplary chart illustrating various conditions of an article under test.

During the experiments, two types of damage were produced onto the hose, rubber layer damage and reinforcement wire damage. The voltage input for constant voltage amplitude is illustrated in FIG. 18. The output of sensor receiver under three conditions, no damage, rubber cover damage and reinforcement wire damage is displayed in FIG. 19. The wire damage in the hose is around 20 wires. A significant voltage drop is observed for both damage types, with higher voltage drop for wire damage. The same measurement is done for a linearly increased voltage input, as seen in FIG. 20. The output response for the three damage cases is shown in FIG. 21. Table III gives a comparison of the voltage output for two types of input. As seen in the table, voltage inputs are not equal (40V and 15V).

TABLE III

Output response comparison from constant amplitude and linearly increasing amplitude inputs.

| Constant Amplitude | | | Linearly Increasing Amplitude | | |
|---|---|---|---|---|---|
| No Damage | 40 | 2 | No Damage | 15 | 0.12 |
| Rubber Layer Damage | 40 | 0.8 | Rubber Layer Damage | 15 | 0.08 |
| Wire Damage | 40 | 0.35 | Wire Damage | 15 | 0.02 |

Figures 22A, 22B, 22C:
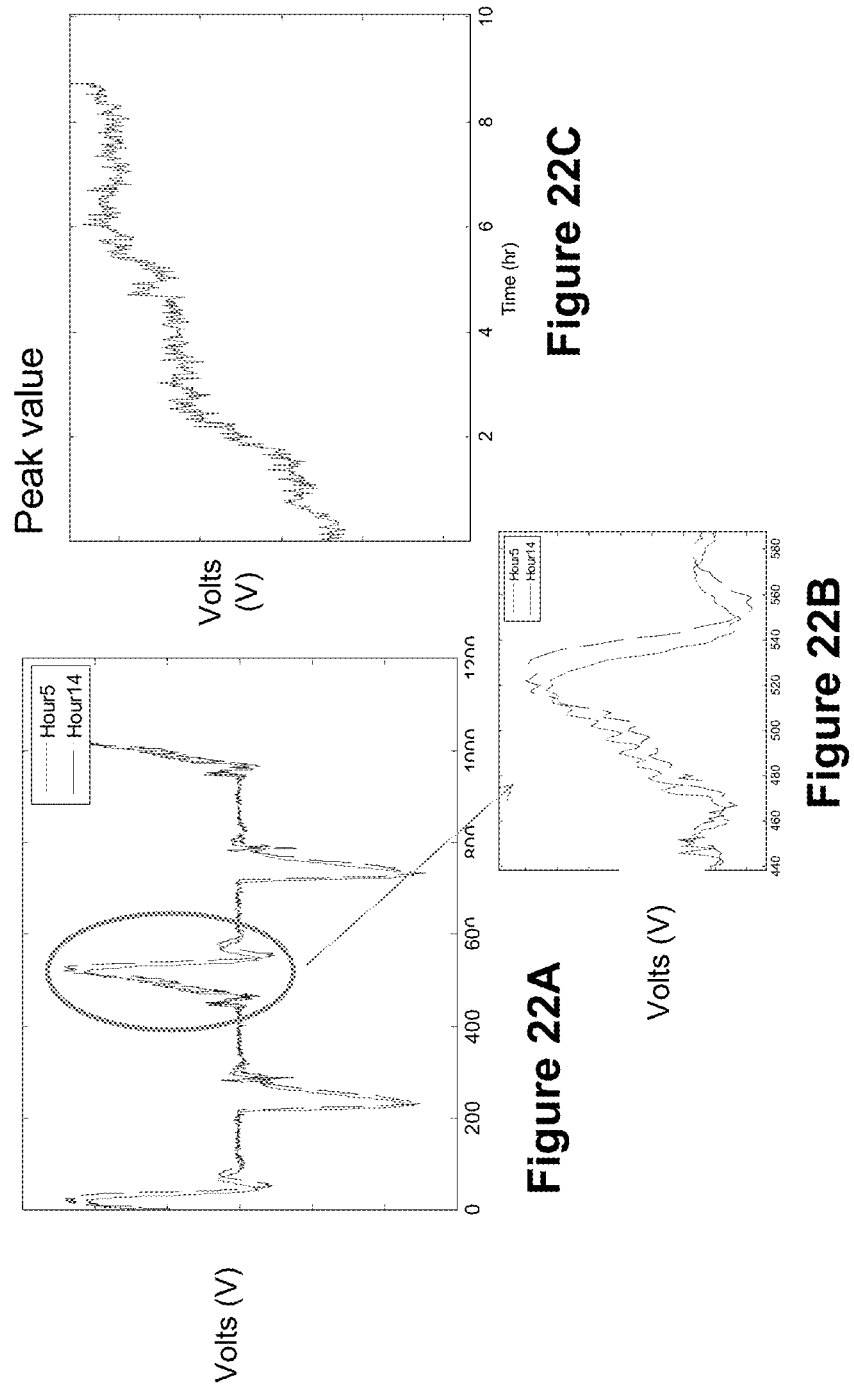
FIGS. 22A-22C are exemplary charts illustrating time domain analysis of signals received from the sensing element.

In summary, damage in the article (e.g., in the rubber and steel) produce results that are detectable by the sensor. For example, by looking at the time domain signal received from the sensor 10, as illustrated in FIGS. 22A-C, it may be seen that the voltage output increases and/or decreases as the article wears. Such changes may result due to the outside diameter change of the article. Referring to FIG. 22A, a time domain signal comparison is illustrated for articles having various ages. In FIG. 22B, is an exploded view of FIG. 22A and FIG. 22C illustrates the peak values over a ten (10) hour period.

Figure 23:
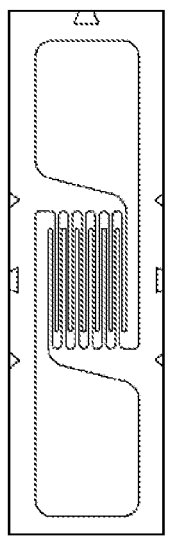
FIG. 23 is an exemplary sensing element in accordance with aspects of the present invention.
Figure 24:
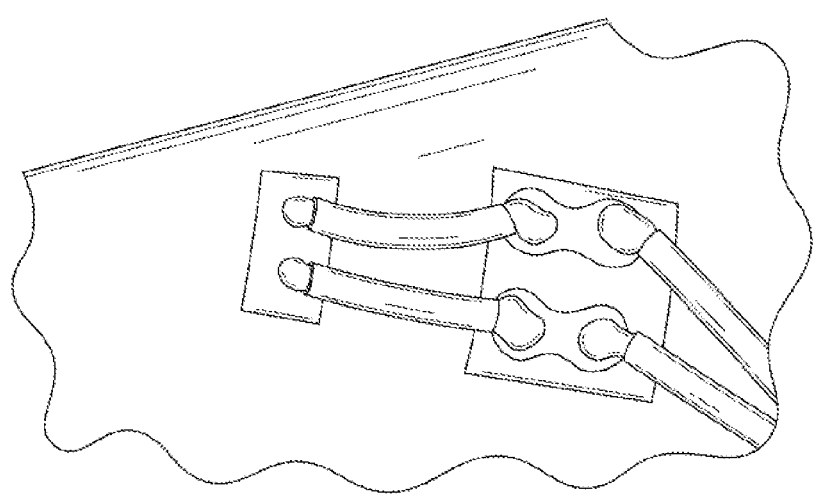
FIG. 24 is an exemplary illustration of the sensing element of FIG. 23 coupled to an article.

As set forth above, a strain gauge may be used as a sensing element 12 in accordance with aspects of the present invention. An exemplary strain gauge is illustrated in FIG. 23. The strain gauge may be used to detect damage in the wire layers in the article (A), for example. A spiral strain gauge bonded to a continuous wire layers in the spiral hose will provide a continuous strain signal. An exemplary strain gauge bonded to the article is illustrated in FIG. 24. If there is damage in the wire layer, it will disrupt the continuity of the wire layers. The discontinuity will affect the strain in the hose; as a result the strain signal from the damage layer will be comparatively different from the healthy condition. So, by monitoring the strain signal of the hose, it is possible to identify the onset of any damage in the wire layer in a spiral hose.

Exemplary strain gage parameters include, for example, Gage Series EA, Gage Resistance 120Ω, Gage Length 0.031", Overall Pattern Length 0.140", Grid Width 0.032", Overall Pattern Width 0.032", Matrix Length 0.27", Matrix Width 0.12". As illustrated in FIG. 24, the miniature strain gage was bonded to the spiral hose using a non-conductive epoxy. The strain gage was bonded in the direction that is parallel to the orientation of the steel layers in the hose.

A data acquisition module (e.g., a NI 9215 from Data Acquisition) was used to acquire the strain readings from the gage. Two different tests were conducted. In the first test, the spiral hose in the healthy condition was bent and the strain signal was obtained. In the second test, a crack was induced in the steel layers near the strain gauge and the strain signal was obtained when the hose was bent.

Figure 25:
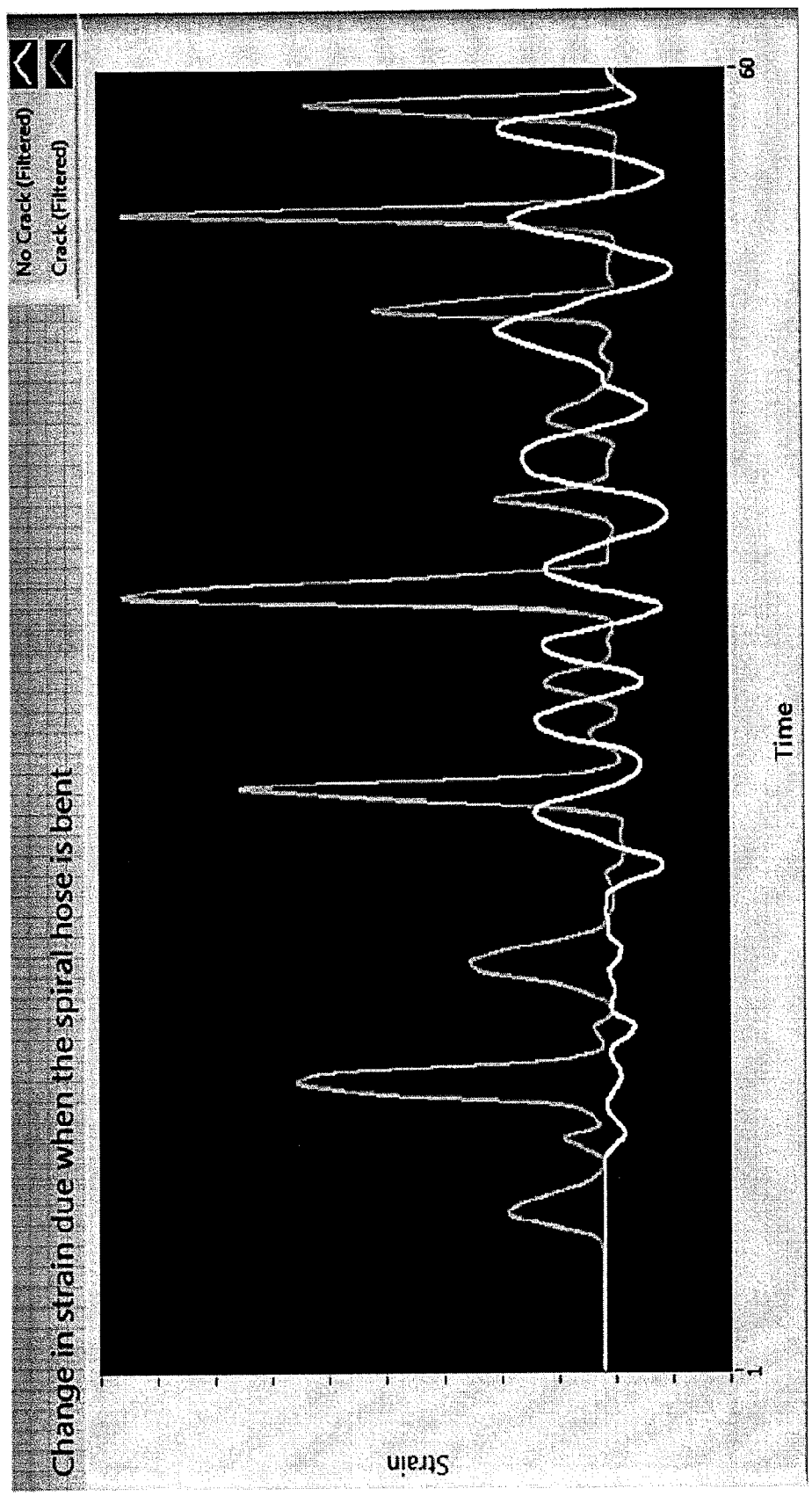
FIG. 25 is an exemplary chart illustrating changes in strain in a healthy article and an article with a defect in accordance with aspects of the present invention.

FIG. 25 illustrates the strain signal obtained from the healthy and the damaged hoses. The lower trace (white) is the signal from healthy hose and the darker trace from the defective hose. As seen from the graph, the signal of the defective hose is comparatively different from the healthy hose. Thus by continuously monitoring the strain signal, it is possible to identify the damage in the hose.

From the experiments conducted, it can be concluded that the discontinuities in the continuous spiral windings can be detected due to change in load transfer. Also, when the strain gages are bonded at the critical locations in the hose, where the failure is more predominant, any damage occurring to the steel layers can be detected in those areas by continuously monitoring the strain signals. This enables the local monitoring at hot spots possible in a spiral hose.

Although the principles, embodiments and operation of the present invention have been described in detail herein, this is not to be construed as being limited to the particular illustrative forms disclosed. They will thus become apparent to those skilled in the art that various modifications of the embodiments herein can be made without departing from the spirit or scope of the invention.

What is claimed is:

1. A sensor system for monitoring health of an associated article, the sensor system comprising:
a sensing element disposed along a length of an outer surface of the associated article, wherein the sensing element is configured to passively detect deflection of an outer surface of the associated article and output an electrical signal in proportion to an amount of deflection;
a mounting mechanism configured to secure the sensing element to at least a portion of the outer surface of associated article; and
a processor communicatively coupled to the sensing element, wherein the processor is configured to:
extract a plurality of different features from deflection data obtained by the sensing element;
generate, using the plurality of different features, an associated distribution of the features, wherein a baseline distribution of the features indicative of normal behavior of the associated article is represented by the baseline distribution in a first position;
generate, utilizing the associated distribution of the features a confidence value, the confidence value indicative of a similarity in position between the associated distribution of features and the baseline distribution of features; and determine the article is damaged or degraded when the confidence value for a deviation from the baseline distribution corresponds to abnormal behavior.

2. The sensor system of claim 1, wherein the sensing element is an electroactive polymer that measures force generated between the mounting mechanism and the outer surface of the associated article.

3. The sensor system of claim 1, wherein the sensing element is a piezoelectric material that measures force generated between the mounting mechanism and the outer surface of the associated article.

4. The sensor system of claim 1, wherein the sensing element is one or more strain sensors that measure deformation of the outer surface of the associated article.

5. The sensor system of claim 1, further including a deformable dielectric layer configured to cover at least a portion of the associated article and the force sensing material.

6. The sensor system of claim 5, wherein the deformable dielectric layer is adhesively affixed to at least a portion of the mounting mechanism.

7. The sensor system of claim 1, wherein the mounting mechanism is releasably secured to the outer surface of the associated article.

8. The sensor system of claim 1, wherein the mounting mechanism is a hose clamp.

9. The sensor system of claim 1, wherein the sensing material is adhesively affixed to at least a portion of the deformable dielectric layer.

10. The sensor system of claim 1, further including a pair of wire leads coupled to the sensing element, wherein the pair of wire leads are configured to output the electrical signal output generated from the sensing element to an external device.

11. The sensor system of claim 1, wherein the sensing element is supported by a deformable substrate and the substrate is operable to conform to at a portion of the outer surface of the associated article.

12. The sensor system of claim 1, wherein the mounting mechanism includes a motion assembly for moving the sensor along a length of the associated article.

13. The sensor system of claim 1, comprising:

a non-transitory storage device coupled to the sensing element, wherein the storage device is configured to store the output of the sensing element and the storage device further includes reference data.

14. The sensor system of claim 13, wherein the non-transitory storage device is wirelessly coupled to the sensing element.

15. The sensor system of claim 13, wherein a prescribed threshold value is stored in the non-transitory storage device and if the processor determines that the output of the sensing element varies by more than the prescribed threshold value, a health indication warning is output to an associated user.

16. The sensor system of claim 1, wherein generating the waveform includes generating the waveform based on at least one of maximum deflection of the outer surface, a minimum deflection of the outer surface, an RMS deflection of the outer surface, or a frequency domain peak of the deflection of the outer surface.

17. The sensor system according to claim 1, wherein the processor is further configured to i) determine a number of strain cycles applied to the article based on the output of the sensing element, and ii) output a health indication based on the number of strain cycles with respect to a prescribed value.

18. The system according to claim 1, wherein the different features include at least one feature in the time domain and at least one feature in the frequency domain.

* * * * *